United States Patent

Takahashi et al.

[11] Patent Number: 5,954,190
[45] Date of Patent: Sep. 21, 1999

[54] ANTIBACTERIAL AND FUNGICIDAL CHAIN

[75] Inventors: Toshio Takahashi, Toyonaka; Koji Tanaka, Osaka; Katsutoshi Shibayama, Higashiosaka; Masaaki Ikeda, Kadoma, all of Japan

[73] Assignee: Tsubakimoto Chain Co., Osaka-fu, Japan

[21] Appl. No.: 08/660,766

[22] Filed: Jun. 10, 1996

[30] Foreign Application Priority Data

Jun. 29, 1995 [JP] Japan ................................. 7-163678

[51] Int. Cl.⁶ ...................................................... B65G 17/06
[52] U.S. Cl. ............................................................ 198/853
[58] Field of Search ................................... 198/850, 851, 198/852, 853

[56] References Cited

U.S. PATENT DOCUMENTS 4,597,747  7/1986  Lapeyre .
4,611,710  9/1986  Mitsufuji .
5,586,643  12/1996  Zabron et al. ........................ 198/853

FOREIGN PATENT DOCUMENTS

| 190 504 | 8/1986 | European Pat. Off. . |
| 0 427 858 | 5/1991 | European Pat. Off. . |
| 0 606 762 | 7/1994 | European Pat. Off. . |
| 44 04 680 | 8/1994 | European Pat. Off. . |
| 43 44 306 | 6/1994 | Germany . |

*Primary Examiner*—James R. Bidwell
*Attorney, Agent, or Firm*—Armstrong, Westerman, Hattori, McLeland & Naughton

[57] ABSTRACT

A chain includes resin links 1 and resin link pins which are formed by molding a mixture of polyacetal as resin material and 0.1 to 5.0% by weight of an inorganic antibacterial agent containing silver such as silver phosphate salt glass, which antibacterial agent is dispersed homogeneously in the resin material. The growth of bacteria and fungi on a chain for conveying products such as food and medicines is suppressed.

2 Claims, 1 Drawing Sheet

5,954,190

ANTIBACTERIAL AND FUNGICIDAL CHAIN

BACKGROUND OF THE INVENTION

1. Field of the Invention

This invention relates to a chain for conveying products which is protected from bacteria and fungi.

2. Description of the Related Art

Chains for conveying food and medicines thereon, the components of which chains are made partially or wholly of resins such as polyacetal, have been widely used. However, such conventional chains are not antibacterial and fungicidal. Therefore, when the chain is used when wet or used in a conveyor line in a humid atmosphere, bacteria and fungi grow on soils on the chain. Such growth is a problem of these conventional chains. To cope with the growth, it is required to sterilize periodically by antibacterial solution, heat, and ultraviolet rays, and to pay sufficient attention to keep products clean.

On the other hand, when antibacterial solution is used for sterilizing products such as food, impact on the human health is not completely avoided. Furthermore, resin components of the chain are deteriorated gradually by acid or chlorine contained in the antibacterial solution. High temperature sterilization and ultraviolet sterilization also deteriorate resin components of the chain disadvantageously.

SUMMARY OF THE INVENTION

The present invention solves the above problems by providing an antibacterial and fungicidal chain in which the chain components comprise a mixture of resin material and antibacterial agent.

BRIEF DESCRIPTION OF THE DRAWINGS

A better understanding of the present invention can be obtained by reference to the drawings, wherein.

DESCRIPTION OF THE PREFERRED EMBODIMENTS OF THE PRESENT INVENTION

Figure 1:
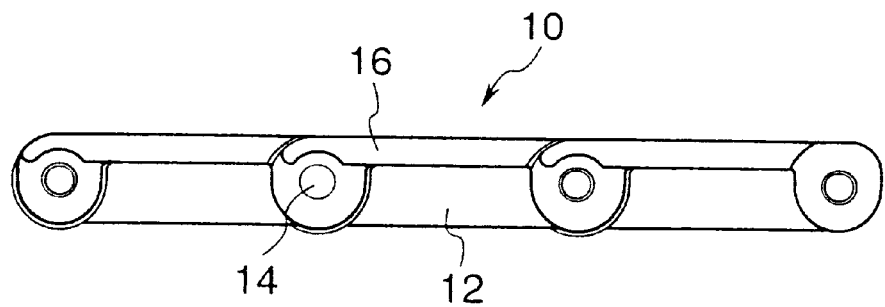
FIG. 1 is a front view of a table top chain to which the present invention is preferably applied.

Chain components in which antibacterial agent is dispersed homogeneously are formed by mixing a resin material and antibacterial agent followed by molding, of the mixture to form the chain components. The component itself is antibacterial and fungicidal, therefore, even when the chain is soiled with water drops and food, the growth of bacteria and fungi is prevented.

Antibacterial agents are categorized to inorganic antibacterial agents and organic antibacterial agents. The sterilization power of inorganic antibacterial agents is strong in the order of antibacterial agents containing mercury, silver, lead, copper, nickel, zinc, and cadmium. Among these agents, inorganic antibacterial agents containing silver scarcely impact on human health and are excellent in safety.

Examples of antibacterial agents containing silver include, for example, silver phosphate salt glass, silver phosphate zirconium, silver zeolite, silver hydro-apatite, and silver phosphate salt ceramics. It may be possible to replace silver of an antibacterial agent with another metal mentioned above.

Preferable examples of organic antibacterial agents include isothiazoline antibacterial agents and benzoic acid antibacterial agents.

In the case of using an inorganic antibacterial agent containing silver, the content of the antibacterial agent is preferably 0.1 to 5.0% by weight to resin material. If the content of an antibacterial agent is less than 0.1% by weight, the sterilizing power is not sufficient. On the other hand, a content of an antibacterial agent exceeding 5.0% by weight results in reduced material properties such as tensile strength, fatigue strength, and impact strength, and the chain can not play a role as chain.

Examples of the present invention will be described hereinafter referring to the drawings. The present invention involves chains for conveying products, mainly such as food and medicines, however, the invention is by no means limited to these applications.

Figure 2:
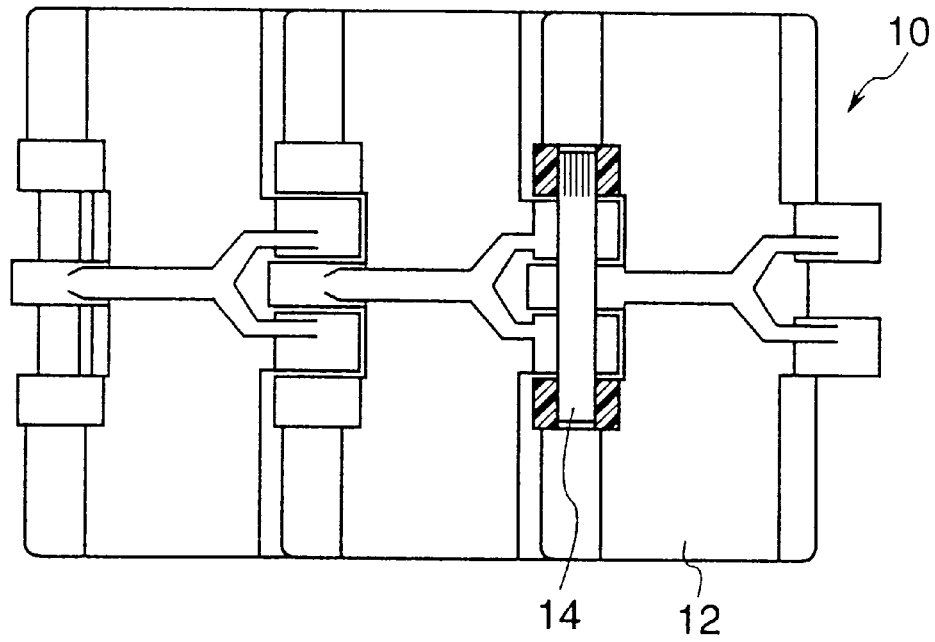
FIG. 2 is a bottom view of the table top chain shown in FIG. 1.

FIG. 1 and FIG. 2 are a front view and bottom view of a table top chain which is suitably used for conveying food. In the figures, a chain 10 has links 12 and link pins 14 as components. Links 12 are of the same shape and are linked with each other by link pins 14 in the conveying direction. The link 12 has a top member 16 with a flat top face. Products such as food are placed directly or indirectly on the top member 16. Links 12 are made of resin material, however, link pins 14 are not necessarily made of resin material because high shearing strength is required and the top member does not contact directly with products. However, it is desirable to form all components of links 12 and link pins 14 with resin material.

In this example, the table top chain for conveying food is described as an example. However, the present invention is not limited to the application of the above-mentioned food conveying and is not limited to the chain type of table top chain.

Another example of chain type includes an accumulation conveyor chain comprising chain components of link plates, link pins, bushes, and rollers. In this case, only some chain components, namely rollers, may be made of the mixture of resin material and antibacterial agent. However, all components may be made of the mixture of resin material and antibacterial agent, and otherwise, rollers and link plates may be made of the mixture of resin material and antibacterial agent.

A popular resin material is polyacetal, and polyacetal resin is used for links 12 in this example. However, polypropylene, polyethylene, polybutylene-terephthalate, polyamide, polyphenylene-ether, and fluoro-resin may be used. Link pins 14 also may be made of these same resins.

Chains 10 of the present invention are made of an above-mentioned resin including an antibacterial agent. Antibacterial agents are categorized to inorganic antibacterial agents and organic antibacterial agents. Inorganic antibacterial agents are preferably used because of excellent heat resistance compared with organic antibacterial agents. The sterilization power of inorganic antibacterial agents is strong in the order of antibacterial agents containing mercury, silver, lead, copper, nickel, zinc, and cadmium. Among these agents the agent which scarcely impacts on human health and is excellent in safety is inorganic antibacterial agents containing silver.

Examples of antibacterial agents containing silver include, for example, silver phosphate salt glass, silver phosphate zirconium, silver zeolite, silver hydro-apatite, and silver phosphate salt ceramics.

Preferable examples of organic antibacterial agents include isothiazoline antibacterial agents and benzoic acid antibacterial agents.

Chain components are formed as described hereinunder. An antibacterial agent is mixed homogeneously with resin material such as polyacetal beforehand. The content of the antibacterial agent is preferably 0.1 to 5.0% by weight to resin material. If the content of an antibacterial agent is less than 0.1% by weight, the sterilizing power is not sufficient. On the other hand, a content of an antibacterial agent exceeding 5.0% by weight results in reduced material properties such as tensile strength, fatigue strength, and impact strength, and the chain cannot play a role as a chain. The mixture of the resin material and antibacterial agent in the prescribed ratio is molded to a desired shape using a molding machine such as injection molding machine. By molding chains as described above, the antibacterial agent is dispersed homogeneously in the resin material, thereby the antibacterial agent will not be lost by evaporation and dissolution. Thus, antibacterial effect and fungicidal effect is active for many years. Possible wearing and cracking of the chain components will not affect adversely on the antibacterial and fungicidal performance.

According to the present invention, an antibacterial agent is contained in resin material, thereby the chain can be used for conveying food without periodical cleaning and sterilization because of antibacterial effect and fungicidal effect of the antibacterial agent. The antibacterial agent is mixed previously with resin material and the mixture is molded to form chain components instead of coating of the antibacterial agent on the chain component. Therefore, the antibacterial agent will not be lost from the chain components by evaporation and dissolution, and the antibacterial effect and fungicidal effect last forever. Chains in accordance with the present invention are suitable for conveying products which must be kept clean. Inorganic antibacterial agents containing silver can be used as the antibacterial agent, and therefore the present invention provides chains used preferably in the field involving human health and hygiene.

The chains containing 0.1 to 5.0% by weight of an antibacterial agent to resin material provide the chains with antibacterial effect and fungicidal effect, and a product conveying capability.

While the invention has been described with the reference to preferred embodiments, it will be appreciated by those skilled in the art that certain modifications may be made without departing from the spirit and scope of the invention defined in the appended claims.

What is claimed is:

1. An antibacterial and fungicidal chain incorporated with chain components, the chain components comprising a mixture of resin material and inorganic antibacterial agent containing silver.

2. A chain as claimed in claim 1, wherein said antibacterial agent is contained in an amount of 0.1 to 5.0% by weight to said resin material.

* * * * *